United States Patent
Noriega et al.

(10) Patent No.: US 6,746,422 B1
(45) Date of Patent: Jun. 8, 2004

(54) STEERABLE SUPPORT SYSTEM WITH EXTERNAL RIBS/SLOTS THAT TAPER

(75) Inventors: Gerardo Noriega, Mountain View, CA (US); Rudolfo Sudaria, Union City, CA (US)

(73) Assignee: Norborn Medical, Inc., Mt. View, CA (US)

( * ) Notice: Subject to any disclaimer, the term of this patent is extended or adjusted under 35 U.S.C. 154(b) by 61 days.

(21) Appl. No.: 09/935,534

(22) Filed: Aug. 22, 2001

Related U.S. Application Data (60) Provisional application No. 60/228,012, filed on Aug. 23, 2000.

(51) Int. Cl.$^7$ .............................................. A61M 31/00
(52) U.S. Cl. .................................................. 604/95.05
(58) Field of Search .......................... 604/93.01, 95.01, 604/95.04, 95.05, 523–536; 600/585, 433–435

(56) References Cited

U.S. PATENT DOCUMENTS

| | | |
|---|---|---|
| 4,068,660 A | 1/1978 | Beck |
| 4,368,730 A | 1/1983 | Sharrock |
| 4,377,169 A | 3/1983 | Banks |
| 4,471,779 A | 9/1984 | Antoshkiw et al. |
| 4,490,421 A | 12/1984 | Levy |
| 4,516,972 A | 5/1985 | Samson |
| 4,534,363 A | 8/1985 | Gold |
| 4,538,622 A | 9/1985 | Samson et al. |
| 4,545,390 A | 10/1985 | Leary |
| 4,548,206 A | 10/1985 | Osborne |
| 4,554,929 A | 11/1985 | Samson et al. |
| 4,573,470 A | 3/1986 | Samson et al. |
| 4,586,923 A | 5/1986 | Gould et al. |
| 4,601,705 A | 7/1986 | McCoy |
| 4,613,385 A | 9/1986 | Thomas et al. |
| 4,616,653 A | 10/1986 | Samson et al. |
| 4,619,263 A | 10/1986 | Frisbie et al. |
| 4,641,654 A | 2/1987 | Samson et al. |
| 4,646,719 A | 3/1987 | Neuman et al. |
| 4,646,742 A | 3/1987 | Packard et al. |
| 4,676,249 A | 6/1987 | Arenas et al. |
| 4,708,717 A | 11/1987 | Deane et al. |
| 4,708,718 A | 11/1987 | Daniels |
| 4,715,378 A | 12/1987 | Pope, Jr. et al. |
| 4,717,387 A | 1/1988 | Inoue et al. |
| 4,719,924 A | 1/1988 | Crittenden et al. |
| 4,721,117 A | 1/1988 | Mar et al. |
| 4,723,936 A | 2/1988 | Buchbinder et al. |
| 4,739,768 A | 4/1988 | Engelson |
| 4,763,647 A | 8/1988 | Gambale |
| 4,767,400 A | 8/1988 | Miller et al. |
| 4,779,628 A | 10/1988 | Machek |
| 4,798,598 A | 1/1989 | Bonello et al. |
| 4,832,047 A | 5/1989 | Sepetka et al. |
| 4,846,186 A | 7/1989 | Box et al. |
| 4,899,787 A | 2/1990 | Ouchi et al. |
| 4,906,241 A | 3/1990 | Noddin et al. |
| 4,925,445 A | 5/1990 | Sakamoto et al. |
| 4,940,062 A | 7/1990 | Hampton et al. |
| 4,953,553 A | 9/1990 | Tremulis |
| 5,021,044 A | 6/1991 | Sharkawy |
| 5,041,085 A | 8/1991 | Osborne et al. |
| 5,059,851 A | 10/1991 | Corl et al. |
| 5,060,660 A | 10/1991 | Gambale et al. |
| 5,067,489 A | 11/1991 | Lind |

(List continued on next page.)

*Primary Examiner*—LoAn H. Thanh
(74) *Attorney, Agent, or Firm*—Townsend and Townsend and Crew, LLP (57) ABSTRACT

A steerable coil working channel system for accessing stenosis, partial occlusions, or complete occlusions within a body lumen. The working channel system generally includes an coiled elongate member such as a hollow guidewire that can be advanced through tortuous regions in the vasculature. A deflectable distal tip is coupled to a distal end of the elongate body to facilitate directionality and positioning of the distal end of the working channel at the target site and steering the elongate body through the tortuous regions in the vasculature.

20 Claims, 6 Drawing Sheets

U.S. PATENT DOCUMENTS

| | | |
|---|---|---|
| 5,107,852 A | 4/1992 | Davidson et al. |
| 5,144,959 A | 9/1992 | Gamble et al. |
| 5,165,421 A | 11/1992 | Fleischhacker et al. |
| 5,176,661 A | 1/1993 | Evard et al. |
| 5,178,158 A | 1/1993 | de Toledo |
| 5,184,627 A | 2/1993 | de Toledo |
| 5,195,971 A | 3/1993 | Sirhan |
| 5,209,727 A | 5/1993 | Radisch, Jr. et al. |
| 5,211,636 A | 5/1993 | Mische |
| 5,217,482 A | 6/1993 | Keith |
| 5,250,034 A | 10/1993 | Appling et al. |
| 5,267,979 A | 12/1993 | Appling et al. |
| 5,306,252 A | 4/1994 | Yutori et al. |
| RE34,695 E | 8/1994 | Mar et al. |
| 5,345,945 A | 9/1994 | Hodgson et al. |
| 5,368,035 A | 11/1994 | Hamm et al. |
| 5,377,690 A | 1/1995 | Berthiaume |
| 5,462,523 A | 10/1995 | Samson et al. |
| 5,484,407 A | 1/1996 | Osypka |
| 5,569,197 A | 10/1996 | Helmus et al. |
| 5,571,085 A | 11/1996 | Accisano, III |
| 5,591,142 A | 1/1997 | Van Erp |
| 5,606,981 A | 3/1997 | Tartacower et al. |
| 5,611,777 A | 3/1997 | Bowden et al. |
| 5,772,609 A | 6/1998 | Nguyen et al. |
| 5,820,591 A * | 10/1998 | Thompson et al. ...... 604/95.01 |
| 5,848,986 A * | 12/1998 | Lundquist et al. ............ 604/22 |
| 5,860,938 A | 1/1999 | LaFontaine et al. |
| 5,865,800 A * | 2/1999 | Mirarchi et al. ......... 604/95.04 |

\* cited by examiner

STEERABLE SUPPORT SYSTEM WITH EXTERNAL RIBS/SLOTS THAT TAPER

CROSS-REFERENCES TO RELATED APPLICATIONS

The present invention claims the benefit of U.S. Provisional Application No. 60/228,012, filed Aug. 23, 2000, the complete disclosure of which is incorporated herein by reference.

The present application is related to U.S. patent application Ser. No. 09/030,657, filed Feb. 25, 1998, now U.S. Pat. No. 6,059,767, the complete disclosure of which is incorporated by reference. The present invention is also related to U.S. Provisional Patent Application No. 60/195,154, filed Apr. 6, 2000, and U.S. Pat. application Ser. No. 09/644,201, filed Aug. 22, 2000 the complete disclosures of which are incorporated herein by reference.

BACKGROUND OF THE INVENTION

The present invention is generally related to medical devices, kits, and methods. More specifically, the present invention provides a system for accessing stenosis, partial occlusions, or total occlusions in a patient's body.

Cardiovascular disease frequently arises from the accumulation of atheromatous material on the inner walls of vascular lumens, particularly arterial lumens of the coronary and other vasculature, resulting in a condition known as atherosclerosis. Atheromatous and other vascular deposits restrict blood flow and can cause ischemia which, in acute cases, can result in myocardial infarction or a heart attack. Atheromatous deposits can have widely varying properties, with some deposits being relatively soft and others being fibrous and/or calcified. In the latter case, the deposits are frequently referred to as plaque. Atherosclerosis occurs naturally as a result of aging, but may also be aggravated by factors such as diet, hypertension, heredity, vascular injury, and the like.

Atherosclerosis can be treated in a variety of ways, including drugs, bypass surgery, and a variety of catheter-based approaches which rely on intravascular widening or removal of the atheromatous or other material occluding the blood vessel. Particular catheter-based interventions include angioplasty, atherectomy, laser ablation, stenting, and the like. For the most part, the catheters used for these interventions must be introduced over a guidewire, and the guidewire must be placed across the lesion prior to catheter placement. Initial guidewire placement, however, can be difficult or impossible in tortuous regions of the vasculature. Moreover, it can be equally difficult if the lesion is total or near total, i.e. the lesion occludes the blood vessel lumen to such an extent that the guidewire cannot be advanced across.

For these reasons, it is desired to provide devices, kits, and methods which can access small, tortuous regions of the vasculature. In particular, it is desired to provide systems which can access partial occlusions, total occlusions, stenosis, blood clots, or thrombotic material. At least some of these objectives will be met by the devices and methods of the present invention described hereinafter and in the claims.

SUMMARY OF THE INVENTION

The present invention provides a hollow guidewire working channel system. The system optionally includes a deflectable distal tip that can allow the hollow guidewire working channel to be steered through the body lumen. The guidewire system of the present invention typically includes an elongate body comprising a proximal end and a distal end. A deflectable distal tip can be coupled to the distal end of the elongate body. The guidewire system optionally includes at least one pull wire that can extend through the elongate body to couple to the distal tip. The pull wire is offset from a longitudinal axis of the distal tip and elongate body, such that axial manipulation of the pull wire deflects the distal tip in a desired direction. By torquing or twisting a proximal end of the hollow guidewire working channel, the deflected tip can be steered and advanced through the tortuous regions of the vasculature.

The hollow guidewire system can be used as a support or access system an can be navigated to and positioned at the target site, with or without the use of a separate guidewire. The hollow guidewire provides the flexibility, maneuverability, torqueability (usually 1:1), and columnar strength necessary for accurately advancing through the tortuous vasculature either over a standard guidewire or on its own. The hollow guidewire working channel has superior strength and rigidity characteristics that are not found in conventional balloon angioplasty or infusion catheters. The hollow guidewire system provides superior physical support for other interventional devices inserted within its lumen as compared to polymeric catheter devices. The hollow guidewire system allows the support of devices used for the dottering (i.e., trying to poke through) of occlusions or stenoses while retaining the desirable characteristics of flexibility, trackability, and torqueability.

The hollow guidewire system can act as a working channel inside of which other interventional devices can be delivered to the target site, such as a rotating guidewire or drive shaft, infusion guidewire, clot maceration guidewire, normal guidewires of varying stiffness, and the like.

Many thin walled polymeric based catheters do not have sufficient maneuverability or torqueability to be advanced through tortuous body lumens on their own and must be navigated to an occlusion over a standard guidewire. In order for these polymeric catheters to be used as working channels, to physically support devices inserted within the catheter lumen intended to penetrate or otherwise treat such lesions, the wall thickness must be increased, which results in a reduction of the size of the inner lumen. In contrast, the hollow guidewire working channel of the present invention typically has a thin wall construction while still providing sufficient torqueability and maneuverability to be advanced through the body lumen, either over a standard guidewire or on its own. Consequently, the thin coil walls allows the lumen of the working channel to be maximized. This allows larger diameter devices to be inserted into the lumen than can be inserted into conventional polymeric based catheters. The larger lumen of the hollow guidewire working channel allows devices such as clot macerators and other larger devices to be delivered to the target lesion. Additionally, the larger diameter lumen of the hollow guidewire allows for infusion of clot dissolving or other fluids, and for aspiration of debris stirred up in the clot maceration process.

Unlike conventional infusion and catheter devices, the hollow guidewire working channel can have a tip which has the same diameter as the rest of the elongate body. Additionally, a radio-opaque marker can be positioned on the extreme distal tip of the catheter. This allows the user to precisely identify the position of the distal tip of the device. Identification of the precise location of the extreme distal tip is advantageous as it allows devices inserted into the working channel to be positioned precisely at the front surface of the occlusion or stenosis.

In some embodiments, the distal tip will optionally have ribs or slots to facilitate deflection in the desired direction. The ribs can be even or tapered.

In use, the hollow guidewire can be advanced through the vasculature to the lesion. Flexing or deflecting the distal tip controls the position and orientation of the devices disposed within the lumen and can avoid perforating the body lumen wall. For example, if the hollow guidewire is navigated to the lesion and the distal tip of the hollow guidewire system is pointed in a direction toward the vessel wall, the direction of the distal tip can be changed by deflecting the tip and torquing and twisting the proximal end of the hollow guidewire system.

These and other aspects of the invention will be further evident from the attached drawings and description of the embodiments of the invention.

DESCRIPTION OF THE SPECIFIC EMBODIMENTS

Figure 1:
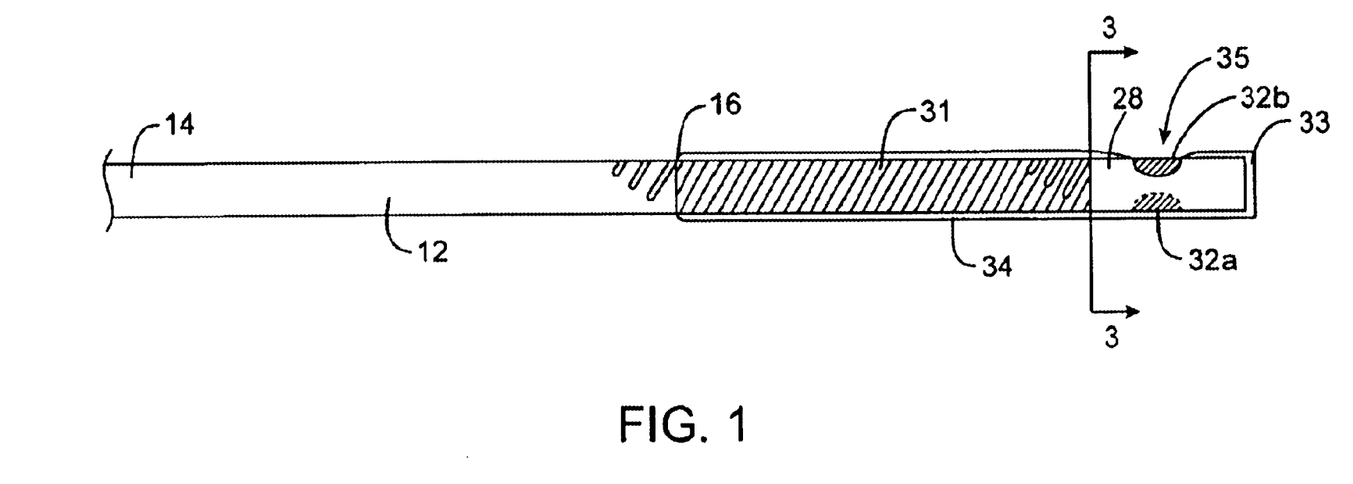
FIG. 1 shows a steerable guidewire system of the present invention.

FIG. 1 shows a steerable guidewire system 10 of the present invention. The steerable guidewire system 10 includes an elongate body 12 having a proximal portion 14 and a distal portion 16. The elongate body 12 preferably has the flexibility, pushability, and torqueability to allow a user to advance the hollow guidewire directly through a tortuous blood vessel to the target site. Because of the high columnar strength of the elongate body 12 there is typically no need for a separate guidewire. Most embodiments of the steerable guidewire system 10 includes a deflectable tip which provides improves the directional control of the hollow guidewire system and any device disposed within the lumen of the system.

Steerable guidewire 10 is typically sized to be inserted through coronary, neuro, or peripheral arteries and can have a variety of diameters. The outer diameter of the hollow guidewire is typically between approximately 0.014 inches and 0.039 inches and preferably between approximately 0.021 inches and 0.039 inches. The length of the hollow guidewire 10 may be varied to correspond to the distance between the percutaneous access site and the target site. For example, for a target site within the heart that is being accessed through the femoral artery, the hollow guidewire will typically have a length of approximately 190 cm. It should be noted however, that other embodiments of the hollow guidewire 10 may have dimensions that are larger or smaller than the above described embodiments and the present invention is not limited to the above recited dimensions.

Figure 2:
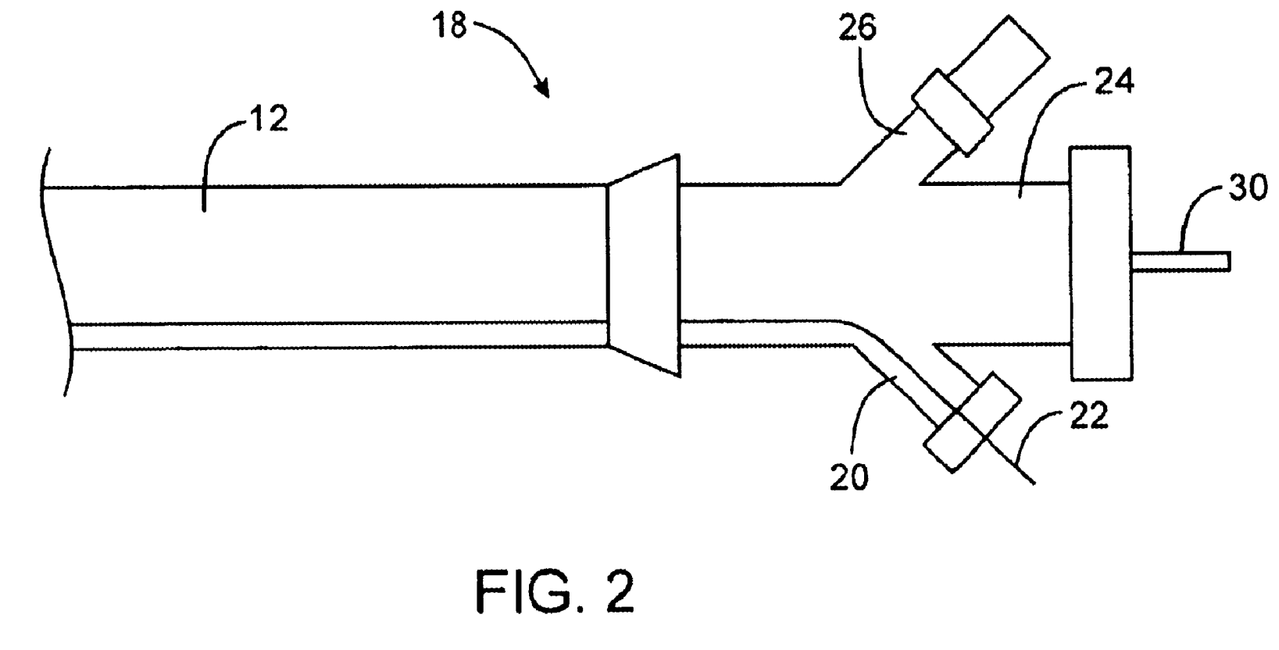
FIG. 2 shows a port assembly of the present invention.

The proximal end of the guidewire 10 can be coupled to a port assembly 18. The port assembly can be a three-armed port assembly. As shown in FIG. 2, the port assembly can include a first arm 20 that houses a steering pull wire 22 that can control the steering of the distal end of the elongate body 12. A second arm 24 can be used to house a drive shaft 30. A third arm 26 can be used to aspirate or infuse the target site. For example, the third arm 26 can be coupled to a vacuum or a medical fluid source.

Referring again to FIG. 1, the hollow guidewire typically has an helically wound elongate body 12 which defines an axial lumen that can be used for infusion or aspiration and that can receive a rotating guidewire, infusion guidewire, clot maceration guidewire, normal guidewires of varying stiffness, devices for treating lesions, and the like. The elongate body includes a proximal tube 14, an intermediate elongate coil body 31, and a distal flexible tip 28. In some embodiments the intermediate elongate coil body 31 is made of stainless steel or nitinol, and the distal tip 28 is composed of stainless steel or nitinol. As shown, the intermediate elongate coil body 31 is threadedly engaged with the proximal portion of distal tip 28 and the distal end of the proximal tube 14. It will be appreciated, however, that the proximal tube 14, intermediate elongate coil body 31, and distal tip 28 can be connected to each other by any other conventional means, e.g. solder, adhesive, or the like.

In some embodiments the distal tip is approximately one half centimeter in length and steerable in one direction. In other embodiments, the distal tip 28 can be steerable in two directions, three directions, four directions, or the like. A devices for treating lesions can be disposed within the lumen of the elongate body so that it can be axially moved and rotated to remove material from the body lumen (not shown). A radio-opaque marker such as platinum-iridium 33 can be positioned at the distal tip to improve visibility under fluoroscopy.

Figure 3:
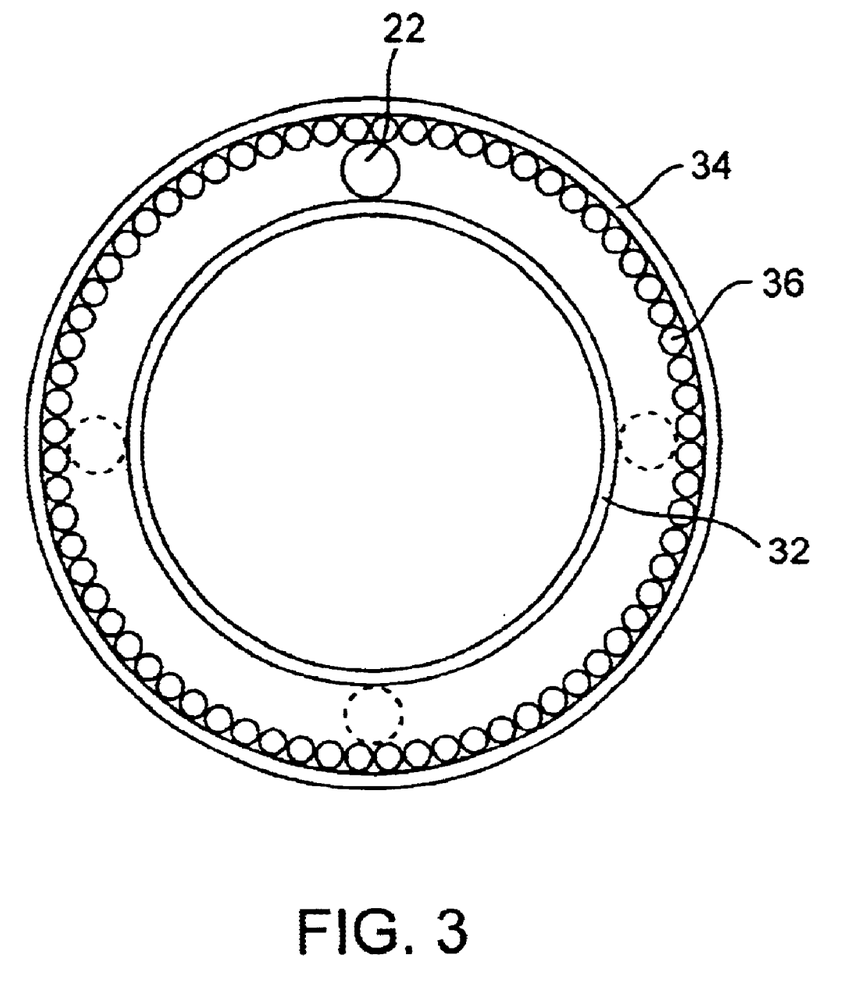
FIG. 3 is a cross sectional view of the distal tip along line 3—3.

Referring now to FIG. 3, a cross section of one embodiment of the steerable guidewire working channel system 10 is shown. An inner tube 32 and outer tube 34 are positioned around a coil 36 and at least a portion of the distal tip 28 to provide a flexible, structural support which prevents liquids from moving between the blood vessel and the axial lumen of the elongate member 12. The outer tube 34 can be shaped to have an elbow opening 35 (FIG. 1) that facilitates bending of the distal tip 28 in the direction of the elbow opening 35. The inner tube 32 is typically polyimide tubing having a 0.001 inch thick wall and may be coated with Teflon® to improve movement of devices through the inner tube 32. The active pull wire(s) 22 can be positioned between the inner tube 32 and the coils 36 to provide for deflection or steering of the distal tip 28.

Deflection of the distal tip is controlled by the user actuated pull wire 22. The pull wire 22 typically extends from the port assembly 18 through the elongate body 12 and connects to the distal end of the tip 28. The pull wire 22 can extend parallel and offset from a longitudinal axis of the elongate body, such that axial actuation of the pull wire can deflect the distal tip in the direction of the pull wire 22. As shown in phantom in FIG. 3, in some embodiments a plurality of pull wires 22 can be positioned around the longitudinal axis of the elongate body to provide a distal tip that is deflectable in multiple directions.

In an exemplary embodiment, the pull wire 22 has a diameter between 0.003 inches and 0.007 inches and is composed of 304SS Hyten®. The pull wire preferably can withstand more than 400 kpsi of tensile force. It should be appreciated however, that the pull wire can be modified to have a smaller or larger diameter and can be made from an alternative material. For example, the pull wire can be comprised of a strip of stainless steel that can be moved axially to steer the distal tip. In one configuration, the pull wire 22 is soldered or otherwise connected to the distal end of flexible tip 28 and the remainder of the pull wire 22 extends proximally to the housing port assembly 18. To reduce the profile of the distal tip 28 and to increase the area of contact between the distal tip and the pull wire, the distal end of the pull wire can be flattened.

Manipulation of the proximal end of the pull wire 22 allows the user to deflect or steer the distal tip 28 without permanently impairing the inner structure of the guidewire 10. The deflectable distal tip provides a user with greater intraluminal control of navigating and steering the hollow guidewire to the target site. In other configurations, the pull wire is 22 can be soldered or otherwise connected to both the distal end and to the junction between the coil 36 and distal tip 28. Therefore, if the tip 28 breaks, the attached pull wire 22 can prevent the tip 28 from detaching from the system 10. A more complete description of the hollow guidewire can be found in commonly owned U.S. patent application Ser. No. 09/030,657, filed Feb. 25, 1998, the complete disclosure of which was previously incorporated by reference.

Figure 4:
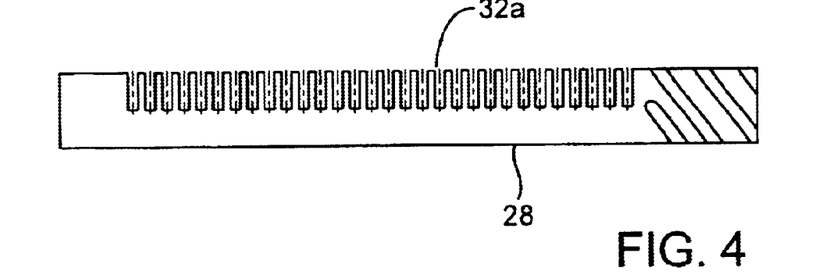
FIG. 4 shows a distal tip having ribs.
Figure 5:
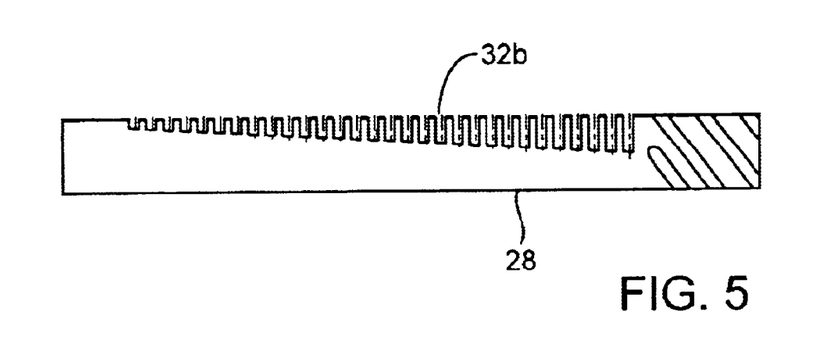
FIG. 5 shows an alternative distal tip having tapered ribs.

As shown in FIGS. 4 and 5 the distal tip 28 can be manufactured to have ribs or partial circumferential slots 32a, 32b formed on at least one side of the distal tip. As shown in FIG. 4 the ribs can extend evenly along one side of the distal tip to provide means for deflecting or flexing of the distal tip in the direction of the ribs. It should be appreciated, the size of the distal tip can be varied so as to accommodate larger and smaller body lumens. In the exemplary embodiment shown, there are thirty ribs formed in the distal tip. It should be appreciated that any number of ribs can be created on the distal tip to facilitate steering. While not shown, in other embodiments, the ribs 32a can be formed on opposite sides of the distal tip 28 so as to facilitate deflecting in two directions. Such ribs 32a can be spaced from the opposite ribs so as to not detrimentally effect the structural strength of the distal tip. Additionally, as mentioned above some embodiments of the distal tip 28 can be steerable in four directions or more. Consequently, ribs can be formed in a plurality of places on the distal tip and additional pull wires can be added to facilitate steering in multiple directions.

FIG. 5 shows an alternative embodiment of the distal tip 28 of the guidewire system 10. The ribs 32a, 32b can be tapered towards a distal end of the tip to provide better control the steering of the distal tip. The tapered ribs provide a larger bend radius at the proximal end of the tip 28 while having a smaller bending radius at the distal end. Alternatively, the ribs can be tapered toward a proximal end of the tip (not shown) to provide another variation to the steering of the distal tip. With such a variation, there will be a larger bending radius at the distal end of the tip and a smaller bending radius at the proximal end of the tip 28.

Figure 6:
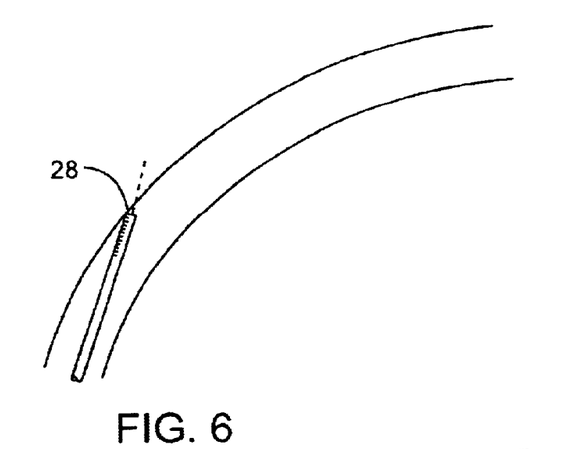
FIGS. 6–8 illustrate a method of advancing the guidewire system through a body lumen.
Figure 7:
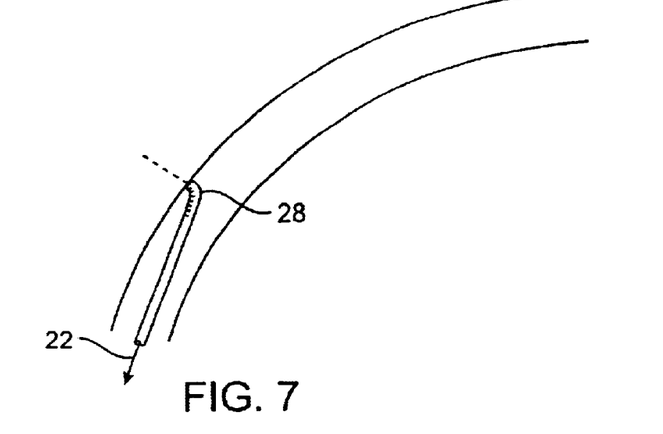
Figure 8:
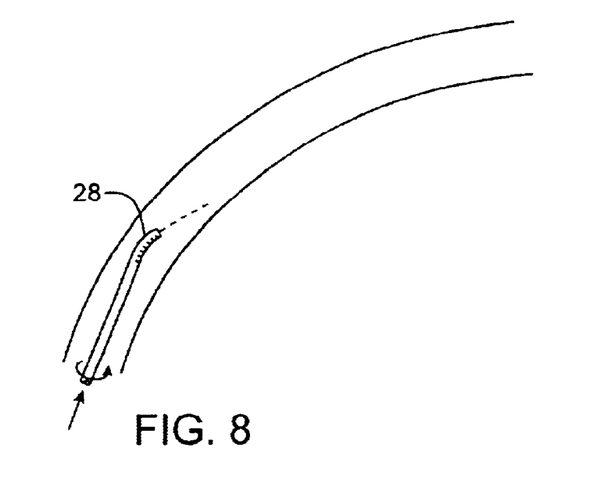

In use, the guidewire can be introduced into the body lumen using conventional delivery techniques. The distal tip can be deflected and/or rotated to navigate through the body lumen to the occlusion. To deflect the distal tip 28, a user will axially move the pull wire 22 until the distal tip is deflected in the desired direction. In exemplary embodiments, the distal tip is deflectable between approximately 5 degrees and 10 degrees. It should be appreciated however, that in other embodiments it may be possible to steer the distal tip up to 180 degrees. For example, as illustrated in FIG. 6, as the hollow guidewire is being advanced through the body lumen, the distal tip 28 may contact a curved portion of the body lumen wall. As shown in FIG. 7, to get past the curved, tortuous portion of the body lumen, the user can then activate the pull wire to deflect the distal tip to change the direction of advancement (as shown by the dotted line). To continue advancement, the user can twist or torque the proximal end of the hollow guidewire system until the distal tip is clear of the body lumen wall and aligned with the body lumen (FIG. 8). Thereafter, the user can push the proximal end of the hollow guidewire system and continue advancement through the body lumen to the lesion. When the lesion has been reached, the device within the lumen of the hollow guidewire system can be advanced out of the hollow guidewire system to treat the lesion.

Figure 9:
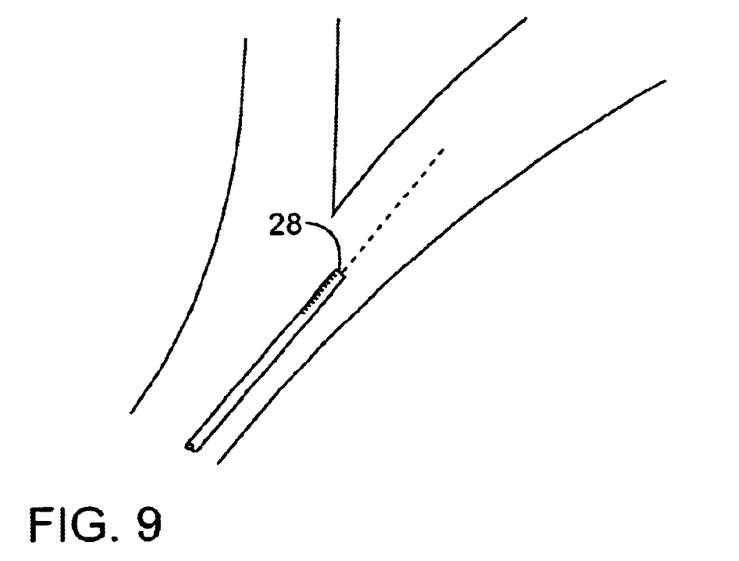
FIGS. 9–10 illustrate advancing through a bifurcated body lumen.
Figure 10:
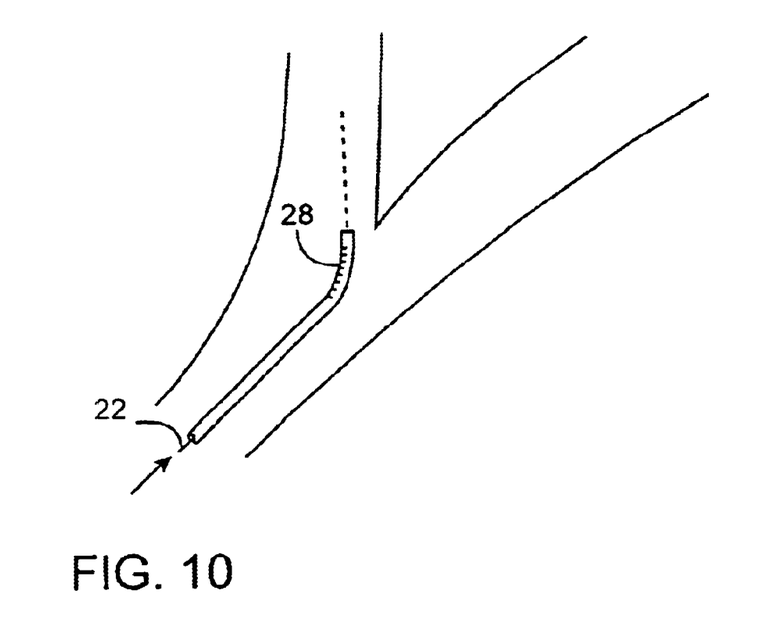

In another method, the deflectable distal tip allows deflection of the distal tip to steer the hollow guidewire system through the correct branch vessel of the body lumen. As shown in FIG. 9, if the guidewire is advanced in its current orientation, the hollow guidewire will be advanced down the right branch vessel. In order to be moved up through the left branch vessel, the tip can be deflected and twisted (if needed) to move the hollow guidewire into alignment with the left branch vessel. Accordingly, in the orientation of the hollow guidewire shown in FIG. 10, advancement of the hollow guidewire will move the hollow guidewire into the left branch vessel.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A steerable support system comprising:
   an elongate body having a lumen extending from a proximal end portion and a distal end portion;
   a deflectable distal tip coupled to the distal portion of the elongate body, wherein the deflectable distal tip comprises ribs that are tapered toward a distal end of the deflectable distal tip;
   a pull wire that extends from the proximal end portion of the elongate body to couple to the deflectable distal tip.

2. The steerable support system of claim 1 wherein the elongate body comprises a hollow guidewire.

3. The steerable support system of claim 1 further comprising a radiopaque marker positioned at a distal end of the deflectable distal tip.

4. The steerable support system of claim 1 wherein a distal end of the pull wire is flattened, wherein the flattened end of the pull wire is attached to the distal tip.

5. The steerable support system of claim 1 further comprising a tubing that covers at least a portion of the elongate body and deflectable tip.

6. The steerable support system of claim 1 wherein the pull wire is moveable and can withstand a tensile force of more than 400 kpsi.

7. The steerable support system of claim 1 wherein the distal tip comprises an open distal end, an open proximal end, and a lumen therebetween, wherein the open proximal end of the distal tip is in communication with the lumen of the elongate body.

8. The steerable support system of claim 1 wherein the distal tip comprises a coil disposed between an inner tube and an outer tube.

9. The steerable support system of claim 1 wherein the elongate body comprises a helically wound coil.

10. A steerable guidewire system comprising:
    an elongate body comprising a lumen, a proximal end, and a distal end; a flexible distal tip coupled to the distal end, wherein the deflectable distal tip comprises ribs that are tapered toward a distal end of the deflectable distal tip; and a deflection wire that extends from the proximal end of the elongate body to the flexible distal tip, wherein the deflection wire controls the deflection of the distal tip.

11. The steerable guidewire of claim 10 herein the deflection wire is deflectable in at least one direction.

12. The steerable guidewire of claim 10 wherein the flexible distal tip is at least partially opaque.

13. The steerable guidewire of claim 10 wherein the flexible distal tip comprises an open distal end.

14. The steerable guidewire of claim 10 wherein the flexible distal tip comprises a coil disposed between an inner tube and an outer tube, wherein the deflection wire is positioned between the coil and the inner tube.

15. A steerable support system comprising:

an elongate coil body comprising a lumen;

a steerable distal tip coupled to a distal end of the elongate coil body, wherein the distal tip comprises a plurality of ribs that are tapered toward a distal end of the distal tip on at least one side of the distal tip; and one or more steering elements that are configured to steer the distal tip in one or more directions.

16. The steerable support system of claim 15 wherein the ribs are comprised of partial circumferential slots in the distal tip.

17. The steerable support system of claim 15 wherein the one or more steering elements comprise an elongate pull wire that is attached to the distal tip at one or more points and extends proximally down a length of the distal tip and elongate coil body.

18. The steerable support system of claim 15 wherein the steerable distal tip is threadedly engaged with the elongate coil body.

19. The steerable support system of claim 15 wherein the distal tip comprises a radiopaque marker.

20. The steerable support system of claim 15 further comprising a port assembly that is in communication with the lumen of the elongate coil body.

* * * * *